United States Patent
Olson et al.

(10) Patent No.: US 10,945,808 B2
(45) Date of Patent: Mar. 16, 2021

(54) CLEANING SYSTEMS FOR REPROCESSING SURGICAL INSTRUMENTS

(71) Applicant: COVIDIEN LP, Mansfield, MA (US)

(72) Inventors: Jessica E. C. Olson, Frederick, CO (US); James D. Allen, IV, Broomfield, CO (US); Stephen J. Stamm, Wheat Ridge, CO (US); Purvishkumar H. Soni, Longmont, CO (US); Alyssa M. Sawyer, Broomfield, CO (US)

(73) Assignee: COVIDIEN LP, Mansfield, MA (US)

( * ) Notice: Subject to any disclaimer, the term of this patent is extended or adjusted under 35 U.S.C. 154(b) by 355 days.

(21) Appl. No.: 15/959,747

(22) Filed: Apr. 23, 2018

(65) Prior Publication Data

US 2019/0321130 A1 Oct. 24, 2019

(51) Int. Cl.
*A61B 90/70* (2016.01)
*B08B 3/04* (2006.01)
*A61B 17/32* (2006.01)

(52) U.S. Cl.
CPC ............ *A61B 90/70* (2016.02); *B08B 3/04* (2013.01); *A61B 17/32* (2013.01)

(58) Field of Classification Search
CPC . A61B 90/70; A61B 90/701; A61B 2090/701; B08B 3/04; B08B 3/044; B08B 3/12; A61L 2/18
See application file for complete search history.

(56) References Cited

U.S. PATENT DOCUMENTS 3,770,010 A 11/1973 Raefield
4,193,818 A 3/1980 Young et al.
4,299,244 A 11/1981 Hirai
4,741,351 A 5/1988 Minkin
5,279,799 A 1/1994 Moser
5,308,406 A 5/1994 Wallock et al.
5,310,524 A 5/1994 Campbell et al.
(Continued)

FOREIGN PATENT DOCUMENTS

DE 10248460 A1 4/2004
EP 2666427 A1 11/2013
WO 2012/148266 A1 11/2012

OTHER PUBLICATIONS

European Search Report issued in corresponding application No. EP 15160513.6 dated Nov. 4, 2015.
(Continued)

*Primary Examiner* — Joseph L. Perrin
*Assistant Examiner* — Kevin G Lee
(74) *Attorney, Agent, or Firm* — Carter, DeLuca & Farrell LLP

(57) ABSTRACT

A cleaning fixture for a surgical instrument includes a handle receiving portion configured to receive a housing of a surgical instrument, a shaft receiving portion configured to receive a shaft and an end effector assembly of the surgical instrument, and a knife actuation assembly movably coupled to the handle receiving portion or the shaft receiving portion. The shaft receiving portion extends distally of the handle receiving portion. The knife actuation assembly is configured to selectively actuate a knife trigger assembly of the surgical instrument to advance a knife of the surgical instrument between jaw members of the end effector assembly thereof.

10 Claims, 9 Drawing Sheets

(56) References Cited

U.S. PATENT DOCUMENTS

| | | |
|---|---|---|
| 5,443,801 A | 8/1995 | Langford |
| 5,489,531 A | 2/1996 | Benson |
| 5,505,218 A | 4/1996 | Steinhauser et al. |
| 5,554,228 A | 9/1996 | Giordano et al. |
| 5,711,921 A | 1/1998 | Langford |
| 5,716,454 A | 2/1998 | Carr |
| 5,755,894 A | 5/1998 | Bowman et al. |
| 5,761,069 A | 6/1998 | Weber et al. |
| 5,913,430 A * | 6/1999 | Gobel ............... A61B 50/22 211/70.6 |
| 5,921,256 A | 7/1999 | Barin |
| 5,928,255 A * | 7/1999 | Meade ............... A61B 17/29 600/564 |
| 8,568,666 B2 | 10/2013 | Langford |
| 9,808,324 B2 | 11/2017 | Fagan et al. |
| 9,877,777 B2 | 1/2018 | Anglese et al. |
| 2004/0118440 A1 | 6/2004 | Sasaki et al. |
| 2011/0132404 A1* | 6/2011 | Lutz ............... A61L 2/025 134/19 |
| 2014/0052135 A1 | 2/2014 | Aman et al. |
| 2015/0066009 A1* | 3/2015 | Garrison ............ A61B 18/1445 606/34 |
| 2016/0175062 A1* | 6/2016 | Limon ............... B08B 3/04 134/32 |
| 2016/0338762 A1 | 11/2016 | Krastins et al. |
| 2017/0360527 A1 | 12/2017 | Fagan et al. |

OTHER PUBLICATIONS

"The EVOTECH(TM) Endoscope Cleaner and Reprocessor. The Next Generation in Flexible Endoscope Reprocessing", Advanced Sterilization Products, a Johnson & Johnson Company, Division of Ethicon; AD-53998 Rev. D, Ethicon, Inc. 2008.

Forte et al., "Comparative cost-efficiency of the EVOTECH endoscope cleaner and reprocessor versus manual cleaning plus automated endoscope reprocessing in a real-world Canadian hospital endoscopy setting", BMC Gastroenterology 2011, 11:105.

* cited by examiner

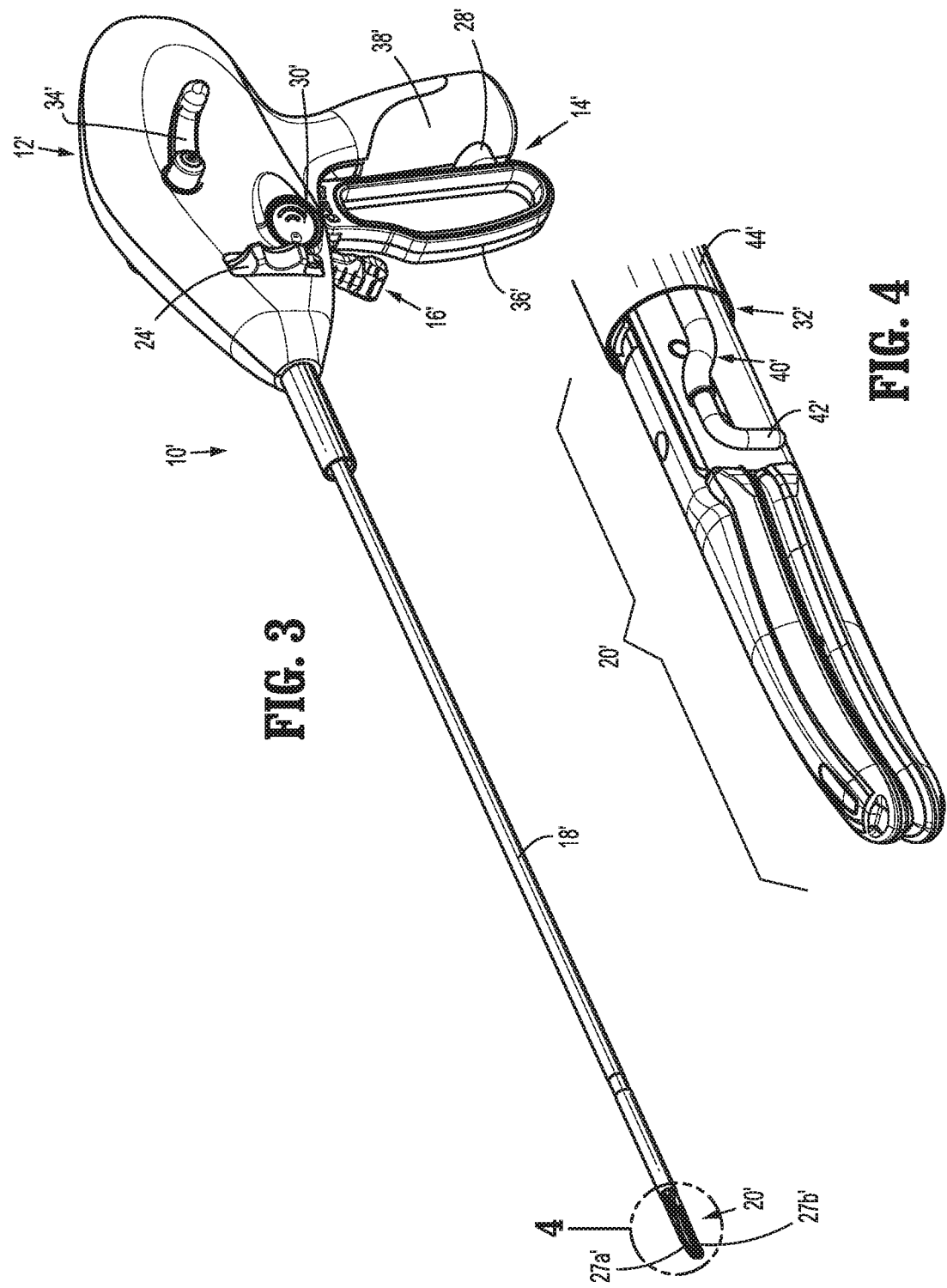

CLEANING SYSTEMS FOR REPROCESSING SURGICAL INSTRUMENTS

BACKGROUND

Technical Field

The present disclosure relates to reprocessing surgical instruments, and more particularly, to systems and methods for reprocessing surgical instruments.

Background of Related Art

Cleaning of medical devices is a known challenge in the field of medical device reprocessing. One challenge in particular is that medical devices usually require substantial disassembly prior to manual or mechanical cleaning. Such disassembly is undesirable because it is a time consuming process, increases the probability of damage, and decreases the fatigue life of the device parts. Another challenge in reprocessing is adequate cleaning. While reprocessing systems typically rely on delivering chemicals and kinetic energy, all surfaces and components of the devices are typically cleaned with the same energy in the same fashion. This is problematic because it can result in inadequate cleaning of the more heavily contaminated areas of the device.

SUMMARY

In accordance with aspects of the present disclosure, a cleaning fixture for a surgical instrument is provided. The cleaning fixture includes a handle receiving portion configured to receive a housing of a surgical instrument, a shaft receiving portion extending distally of the handle receiving portion and configured to receive a shaft and an end effector assembly of the surgical instrument, and a knife actuation assembly movably coupled to the handle receiving portion or the shaft receiving portion. The knife actuation assembly is configured to selectively actuate a knife trigger assembly of the surgical instrument to advance a knife of the surgical instrument between jaw members of the end effector assembly thereof.

In aspects, the knife actuation assembly may include a lever protruding into the handle receiving portion. The lever may be movable relative to the handle receiving portion to actuate the knife trigger assembly of the surgical instrument.

In aspects, the lever may have a proximal end configured to contact the knife trigger assembly of the surgical instrument.

In aspects, the handle receiving portion may be releasably securable with the shaft receiving portion to enclose the surgical instrument therein.

In aspects, the shaft receiving portion may include an elongate muzzle defining a central longitudinal axis and a lumen dimensioned to house the shaft and the end effector assembly of the surgical instrument.

In aspects, the shaft receiving portion may further include a proximal section releasably coupled to a distal section of the handle receiving portion. The elongate muzzle may extend distally from the proximal section.

In aspects, the shaft receiving portion may define an opening disposed towards a distal end portion of the elongate muzzle, such that the opening is positioned adjacent the end effector assembly of the surgical instrument upon receipt of the shaft and end effector assembly of the surgical instrument within the shaft receiving portion.

In aspects, the opening may be configured to facilitate the passage of a cleaning fluid proximally through the elongate muzzle to flush the lumen thereof.

In aspects, the opening may be configured to facilitate the passage of a cleaning fluid proximally towards the knife of the surgical instrument while the knife actuation assembly is actuated.

In aspects, the cleaning fixture may further include a jaw-prop mechanism movably coupled to a distal end portion of the elongate muzzle. The jaw-prop mechanism may include a foot disposed in the lumen of the elongate muzzle and configured to maintain the end effector assembly of the surgical instrument in an open position.

In aspects, the cleaning fixture may further include a lever activation assembly movably coupled to the handle receiving portion or the shaft receiving portion. The lever activation assembly may be configured to selectively actuate a handle assembly of the surgical instrument.

In aspects, the knife actuation assembly may be disposed between an elongate muzzle of the shaft receiving portion and the lever activation assembly.

In further aspects of the present disclosure, a cleaning fixture for a surgical instrument is provided. The cleaning fixture includes a handle receiving portion configured to receive a housing of a surgical instrument, a shaft receiving portion extending distally of the handle receiving portion and configured to receive a shaft and an end effector assembly of the surgical instrument, and a monopolar actuation assembly movably coupled to the handle receiving portion. The monopolar actuation assembly is configured to selectively actuate a monopolar assembly of the surgical instrument to move the monopolar assembly relative to the end effector assembly.

In aspects, the monopolar actuation assembly may be supported on an upper surface of the handle receiving portion.

In aspects, the monopolar actuation assembly may include a lever protruding into the handle receiving portion. The lever may be movable relative to the handle receiving portion to actuate the monopolar assembly of the surgical instrument.

In aspects, the cleaning fixture may further include a lever activation assembly movably coupled to the handle receiving portion or the shaft receiving portion. The lever activation assembly may be configured to selectively actuate a handle assembly of the surgical instrument.

In aspects, the cleaning fixture may be configured to direct a cleaning fluid toward the monopolar assembly of the surgical instrument while the monopolar actuation assembly is actuated.

BRIEF DESCRIPTION OF THE DRAWINGS

Various aspects of the present disclosure are described hereinbelow with reference to the drawings, wherein:

FIG. 3 is a side perspective view of another exemplary embodiment of a surgical instrument suitable for cleaning by the cleaning fixtures of the present disclosure;

FIG. 4 is an enlarged view of the area of detail designated "4" in FIG. 3, illustrating an end effector assembly and a monopolar assembly of the surgical instrument of FIG. 3;

DETAILED DESCRIPTION

As described in more detail below, the present disclosure relates to systems and methods for reprocessing surgical instruments. The cleaning systems provided herein may be used to clean various medical devices, such as, for example, surgical instruments 10, 10' described below. Although exemplary surgical instruments 10, 10' are detailed herein, the present disclosure is equally applicable for use in reprocessing any suitable surgical instrument. As such, the surgical instruments 10, 10' are only summarily described herein.

Figure 1:
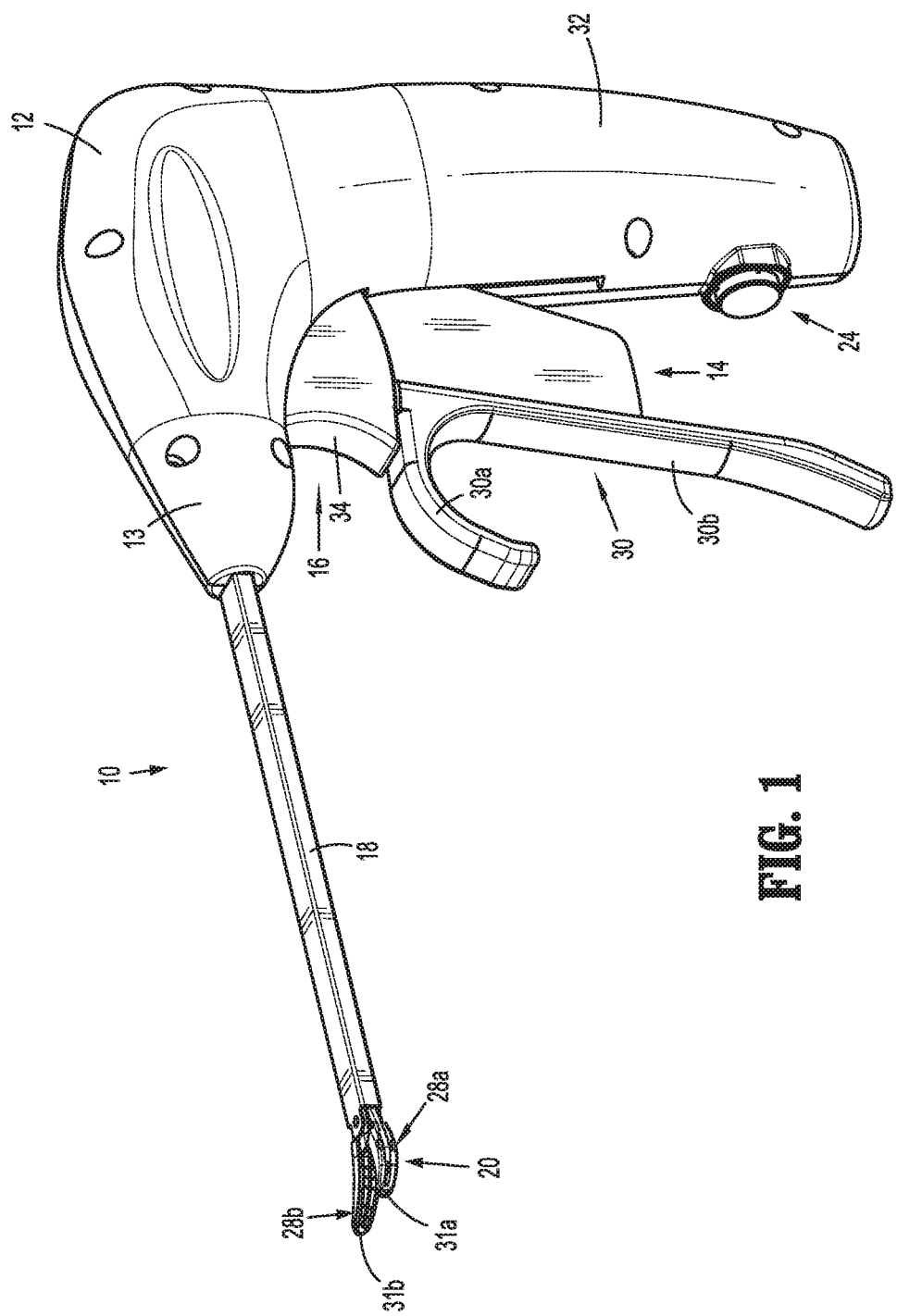
FIG. 1 is a side perspective view of an exemplary embodiment of a surgical instrument suitable for cleaning by the cleaning fixtures of the present disclosure.
Figure 2:
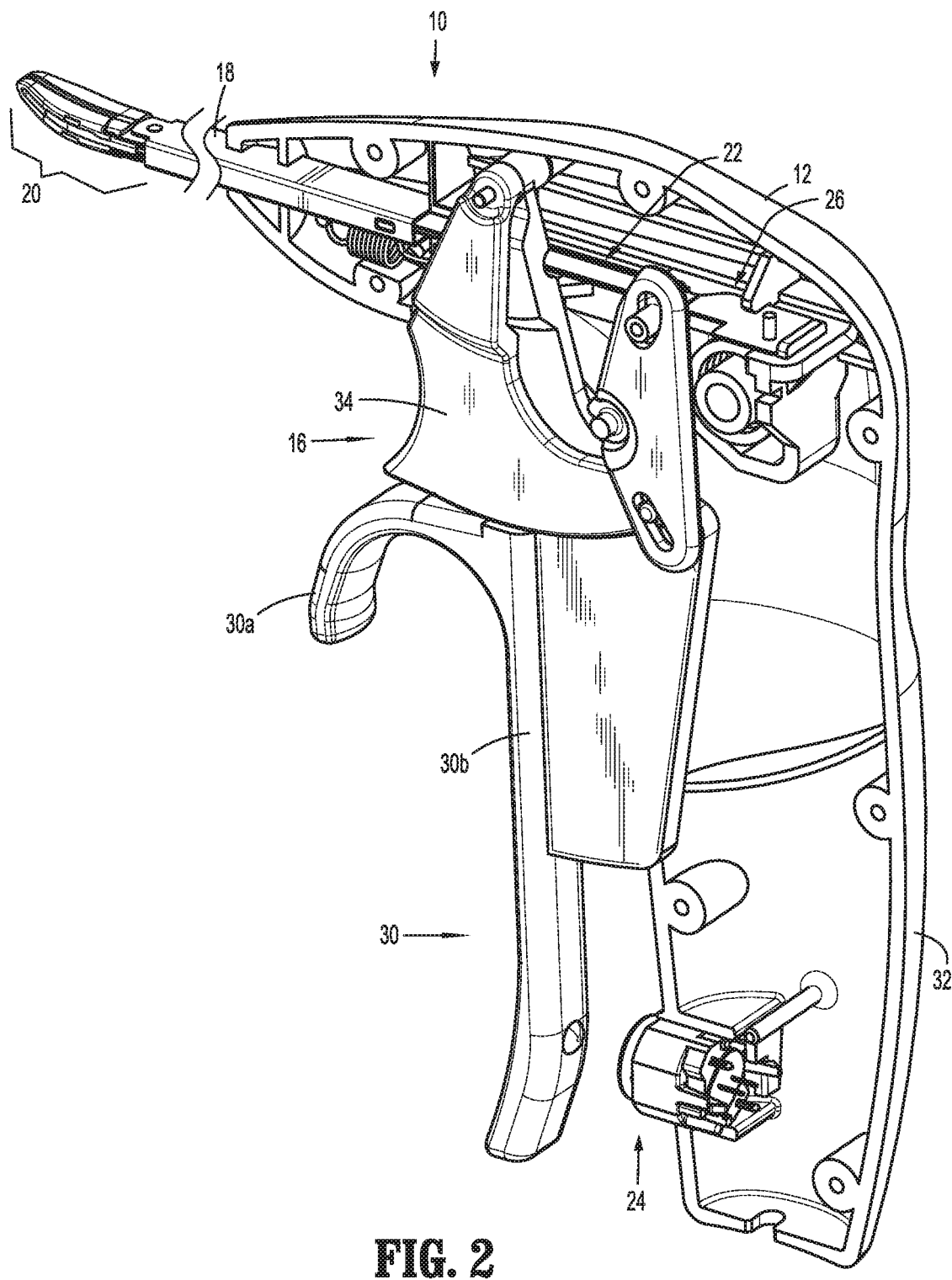
FIG. 2 is a side view of a proximal portion of the surgical instrument of FIG. 1 with a portion of the housing thereof removed to illustrate internal components.

FIGS. 1-2 depict one exemplary surgical instrument 10 that may be cleaned using the cleaning fixtures of the present disclosure. The surgical instrument 10, as described below, is configured for grasping, treating, and/or dissecting tissue.

The surgical instrument 10 generally includes a housing 12, a handle assembly 14, a knife trigger assembly 16, a shaft 18, an end effector assembly 20, a knife 22, and an energy activation assembly 24. The shaft 18 extends distally from the housing 12 and supports the end effector assembly 20 at a distal end thereof. A drive assembly 26 operably couples the handle assembly 14 with the end effector assembly 20, such that an actuation of the handle assembly 14 causes an approximation of a pair of jaw members 28a, 28b of the end effector assembly 20.

The knife 22 is operably coupled with the knife trigger assembly 16 to enable selective translation of a knife blade defined at the distal end of the knife 22 relative to the end effector assembly 20. The energy activation assembly 24 enables energy to be selectively delivered to electrically-conductive surfaces 31a, 31b of jaw members 28a, 28b of the end effector assembly 20 by way of wires (not shown) interconnecting the energy activation assembly 24, the end effector assembly 20, and a generator (not shown) or other suitable energy source. In aspects, the surgical instrument 10 may include an electrosurgical cable (not shown) that connects the surgical instrument 10 to the generator. In alternate aspects, the surgical instrument 10 may be configured as a hand-held instrument including power and energy-generating components disposed on or within housing 12.

The handle assembly 14 of the surgical instrument 10 includes the handle 30 that is movable relative to a fixed handle portion 32 of the housing 12 between an initial position, a compressed position, and an activated position. The handle 30 has an arcuate segment 30a and a proximal leg 30b. In the compressed position, the handle 30 imparts movement of one or both of the jaw members 28a, 28b of the end effector assembly 20 from a spaced-apart position to an approximated position for grasping tissue therebetween and, in the activated position, activates the energy activation assembly 24 to initiate the supply of energy to the end effector assembly 20 for treating grasped tissue.

The knife trigger assembly 16 is operably coupled to the knife assembly 22 to enable selective translation of the knife blade of the knife assembly 22 relative to the end effector assembly 20. Pivoting of a trigger 34 of the knife trigger assembly 16 between an un-actuated position and an actuated position translates the knife blade between respective retracted and extended positions relative to the end effector assembly 20.

In one embodiment, a safety feature may be incorporated into the surgical instrument 10 by which the knife 22 is prevented from being advanced until after the handle assembly 14 is actuated to ensure that the knife 22 is not advanced when the jaw members 28a, 28b are open. In this embodiment, the jaw members 28a, 28b are capable of being clamped to a maximum compression force, at which point the movable handle 30 of the handle assembly 14 is decoupled from the end effector assembly 20, such that the jaw members 28a, 28b are maintained in the spaced-apart position despite further movement of the movable handle 30 towards the compressed position. More specifically, when the maximum compression force is reached, a compression spring of the drive assembly 26 is compressed, decoupling the movable handle 30 from the end effector assembly 20 and allowing further movement of the movable handle 30 towards the compressed position without impacting the position of the jaw members 28a, 28b. Thus, with the end effector assembly 20 held in the spaced-apart position, the movable handle 30 may be moved to the compressed position to clear the knife lockout, thus permitting advancement of the knife 22 despite the end effector assembly 20 being disposed in the spaced-apart position.

For a more detailed description of the features and methods of operation of surgical instrument 10, reference may be made to U.S. Patent Application Publication No. 2016/0338762, filed on May 22, 2015, the entire contents of which are incorporated by reference herein.

Figure 5:
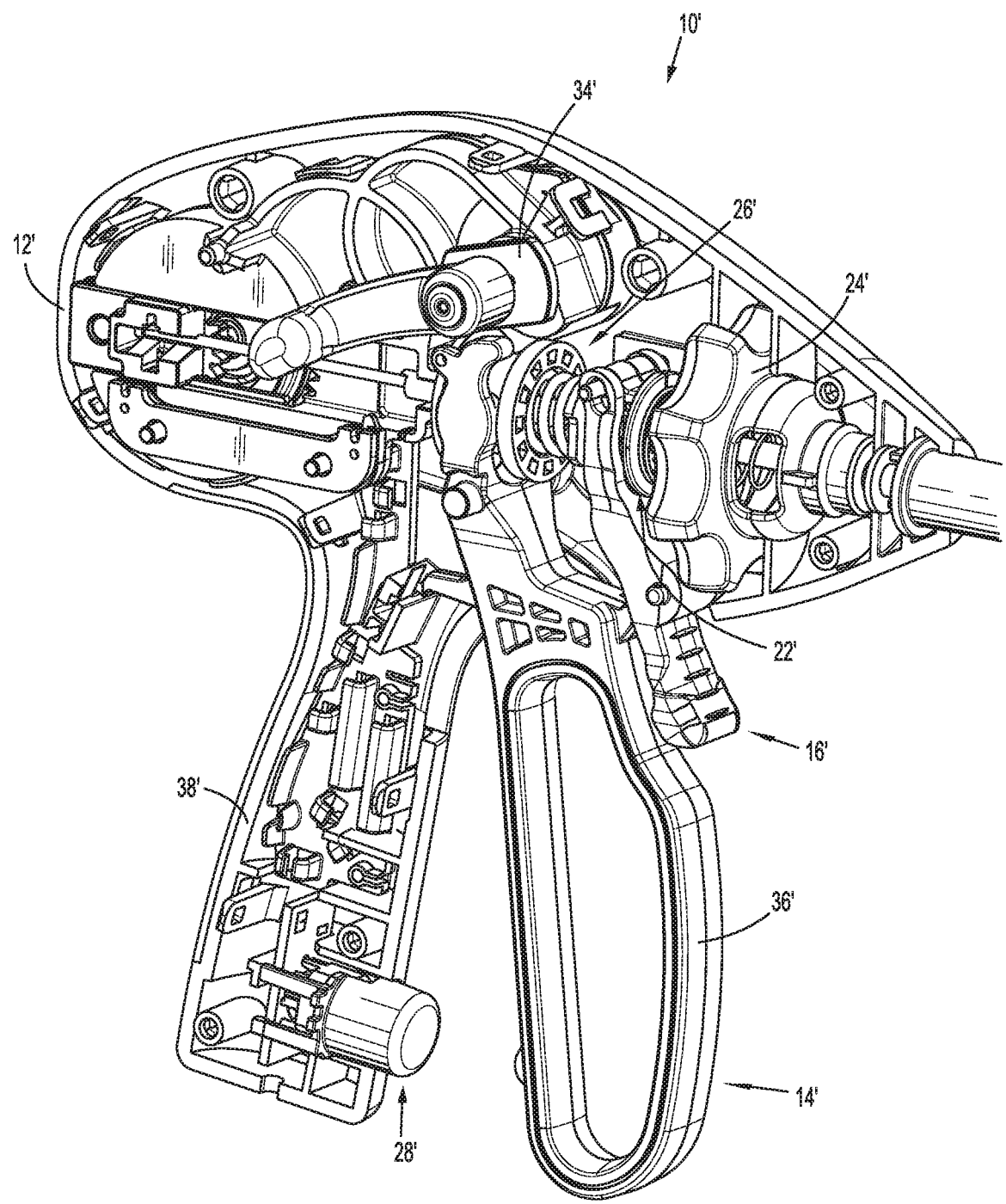
FIG. 5 is a side view of a proximal portion of the surgical instrument of FIG. 3 with a portion of the housing thereof removed to illustrate internal components.

With reference to FIGS. 3-5, another embodiment of a surgical instrument 10' suitable to be cleaned by the cleaning fixtures of the present disclosure is illustrated. The surgical instrument 10' is configured to operate in both a bipolar mode, e.g., for grasping, treating, and/or mechanically dissecting tissue, and a monopolar mode, e.g., for treating and/or electrically/electromechanically dissecting tissue. The surgical instrument 10' generally includes a housing 12', a handle assembly 14', a knife trigger assembly 16', a shaft 18', an end effector assembly 20', a knife assembly 22', a rotating assembly 24', a drive assembly 26', bipolar and monopolar activation assemblies 28', 30', respectively, a monopolar assembly 32', and a deployment and retraction mechanism 34'.

The drive assembly 26' operably couples the handle assembly 14' with the end effector assembly 20' to enable selective manipulation of one or both of the jaw members of the end effector assembly 20'. The knife assembly 22' is operably coupled with the knife trigger assembly 16' to enable selective translation of a knife (not explicitly shown) of the knife assembly 22' relative to the end effector assembly 10'. The deployment and retraction mechanism 34' is operably coupled with the monopolar assembly 32' to enable selective deployment and retraction of the monopolar assembly 32'. The rotating assembly 24' enables selective rotation of the end effector assembly 20' and the monopolar assembly 32' relative to the shaft 18'. The bipolar and monopolar activation assemblies 28', 30' enable the appropriate energy to be selectively delivered to the end effector assembly 20' and the monopolar assembly 32', respectively.

The handle assembly 14' includes a movable handle 36' and a fixed handle 38'. The fixed handle 38' is integrally associated with the housing 12' and the movable handle 36' is movable relative to fixed handle 38' between an initial position, wherein the movable handle 36' is spaced-apart from the fixed handle 38', and a compressed position, wherein the movable handle 36' is compressed towards the fixed handle 38'. Movement of the movable handle 36' toward the fixed handle 38' is configured to approximate the jaw members of the end effector assembly 20'. The shaft 18' extends distally from the housing 12' and supports the end effector assembly 20' at a distal end thereof.

The surgical instrument 10' may include an electrosurgical cable (not shown) that connects the surgical instrument 10' to a generator (not shown) or other suitable power source. In alternate aspects, the surgical instrument 10' may be configured as a battery-powered instrument. The electrosurgical cable (not shown) includes wires (not shown) extending therethrough that have sufficient length to extend through housing 12' and/or shaft 18' in order to provide energy to at least one electrically-conductive surface of the jaw members 27a', 27b' of the end effector assembly 20', e.g., upon activation of a bipolar activation switch of the bipolar activation assembly 28' in the bipolar mode of operation. Similarly, one or more of the wires of the electrosurgical cable (not shown) extends through the housing 12' and/or the shaft 18' in order to provide energy to the monopolar assembly 32', e.g., upon activation of a monopolar activation switch of the monopolar activation assembly 30' in the monopolar mode of operation. As can be appreciated, additional wires (not shown) are provided to electrically couple the various inter-operable electrical components of the surgical instrument 10'.

As best shown in FIG. 4, the monopolar assembly 32' includes an energizable member 40' operably engaged with the deployment and retraction mechanism 34' (FIG. 3) for selectively deploying and retracting the monopolar assembly 32'. The energizable member 40' is coupled to the source of energy (not shown) and the monopolar activation assembly 30' via one or more wires (not shown). The energizable member 40' may be hook-shaped (as shown), or may define any other suitable configuration, e.g., linear, ball, circular, angled, etc. The energizable member 40' is disposed on the inner-edge side of the curved jaw members of the end effector assembly 20' and is movable relative thereto between a storage position, wherein a distal, tissue-treating portion 42' of the energizable member 40' is positioned proximally of the jaw members of the end effector assembly 20', and a use position, in which the distal tissue-treating portion 42' of the energizable member 40' extends distally from a distal end of the end effector assembly 20' to facilitate treating tissue therewith. Energy may be supplied to the distal tissue-treating portion 42' of the energizable member 40', e.g., via activation of either of the activation switches of the monopolar activation assembly 30', for treating tissue in the monopolar mode of operation.

The monopolar assembly 32' further includes an elongated insulative sheath 44' slidably disposed about the shaft 18'. The insulative sheath 44' is selectively movable about and relative to the shaft 18' and the end effector assembly 20' between a storage position, wherein the insulative sheath 44' is disposed proximally of the end effector assembly 20', and a use position, wherein the insulative sheath 44' is substantially disposed about the end effector assembly 20'. The deployment and retraction mechanism 34' is operable to cooperatively translate the insulative sheath 44' and the energizable member 40' between their respective storage positions and use positions.

For a more detailed description of the features and methods of operation of surgical instrument 10', reference may be made to U.S. patent application Ser. No. 14/802,582, filed on Jul. 17, 2015 (now U.S. Pat. No. 9,877,777), the entire contents of which are incorporated by reference herein.

Figure 6:
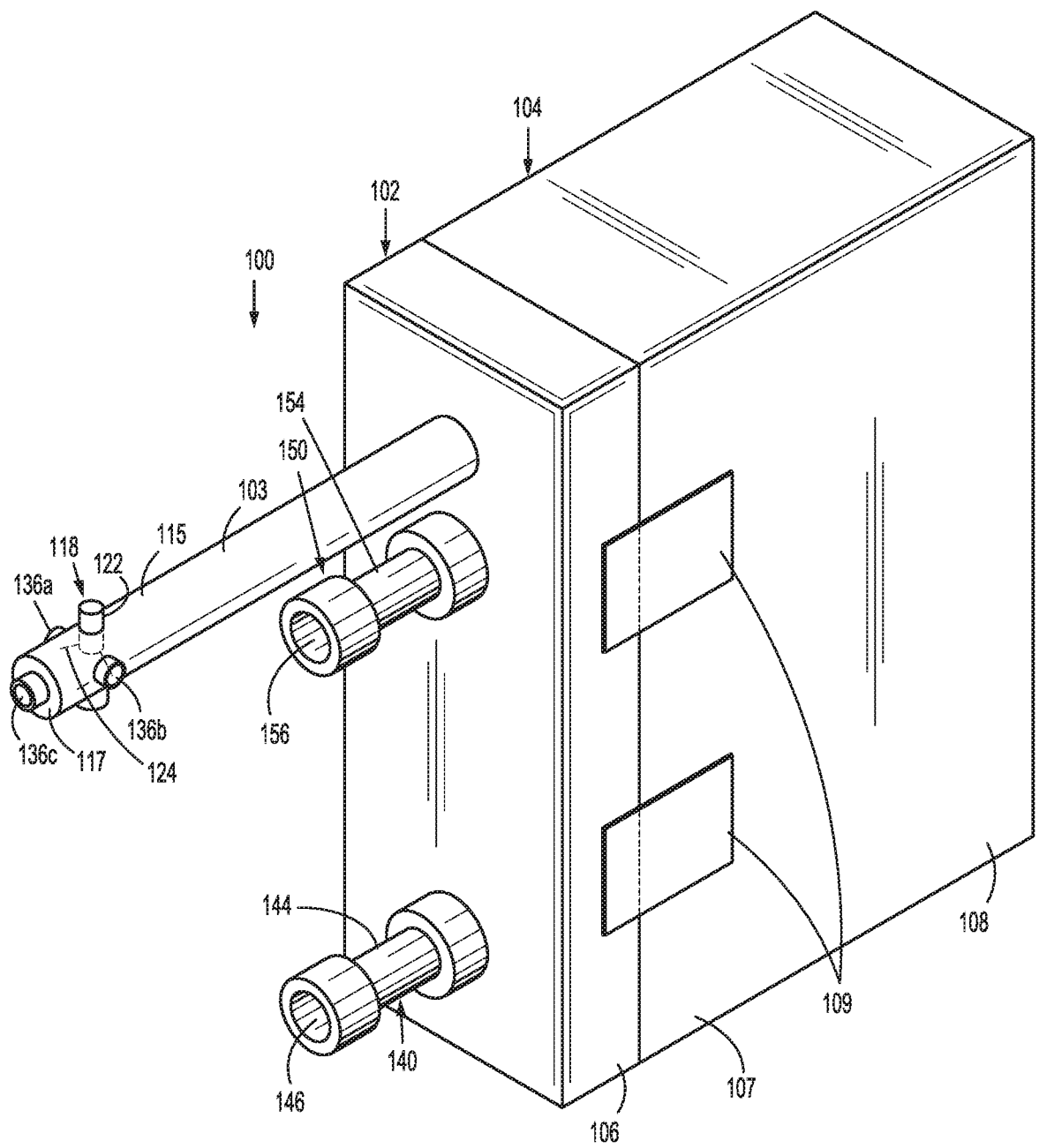
FIG. 6 is a side perspective view of an exemplary embodiment of a cleaning fixture for cleaning the surgical instrument of FIGS. 1-2.
Figure 7:
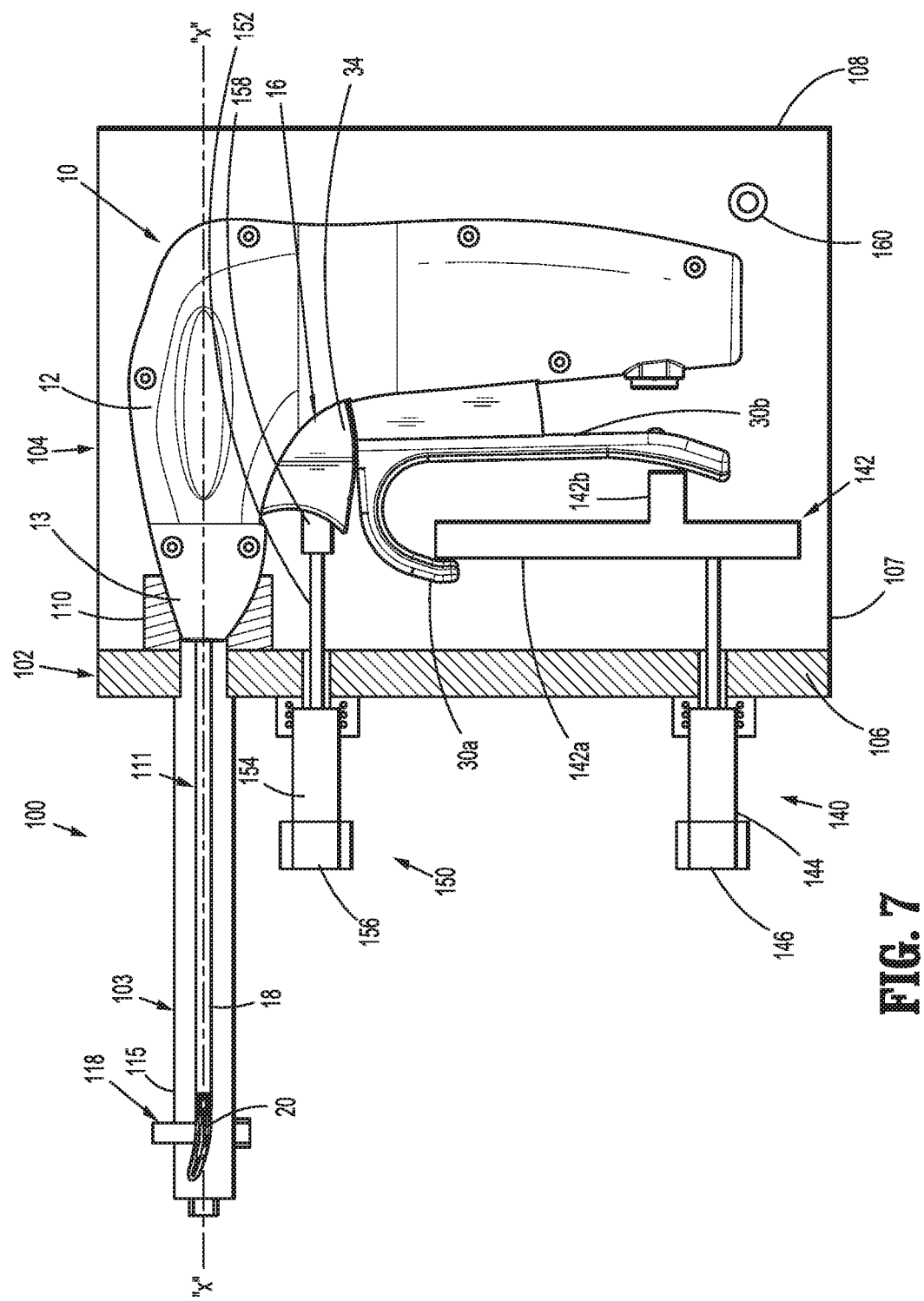
FIG. 7 is a side cross-sectional view of the cleaning fixture of FIG. 6, with the surgical instrument of FIGS. 1-2 disposed therein.

With reference to FIGS. 6 and 7, a cleaning fixture provided in accordance with the present disclosure is shown generally as cleaning fixture 100. The cleaning fixture 100 is shown housing surgical instrument 10 therein (FIGS. 1 and 2) for cleaning of the surgical instrument 10. However, in some aspects, the cleaning fixture 100 may similarly be configured for use with any other suitable surgical instrument. Different configurations and considerations apply in providing a cleaning fixture 100 for a particular type of surgical instrument; however, the aspects and features of the present disclosure remain generally consistent regardless of the particular surgical instrument for which the cleaning fixture 100 is configured. It is also contemplated that a generic cleaning fixture be provided to enable cleaning of any one of a variety of different surgical instruments. Such a generic cleaning fixture may include interchangeable and/or adaptable components configured to achieve various different configurations to accommodate various different surgical instruments.

The cleaning fixture 100 generally includes a shaft receiving portion 102 and a handle receiving portion 104. The shaft receiving portion 102 includes a proximal section 106 that is releasably secured to a distal end section 107 of the handle receiving portion 104. The shaft receiving portion 102 may be detachably coupled to the handle receiving portion 104 via fastening members 109. The fastening members 109 may include latches or any other suitable releasable fastening mechanism. In some aspects, the handle receiving portion 104 and the shaft receiving portion 102 may be hingedly coupled to one another. The proximal section 106 of the shaft receiving portion 102 and the handle receiving portion 104, when fastened to one another, cooperate to define an enclosure for retaining the housing 12, the handle assembly 14, and the knife trigger assembly 16 of the surgical instrument 10, as detailed below.

The shaft receiving portion 102 of the cleaning fixture 100 further includes an elongate muzzle 103 extending distally from the proximal section 106 thereof. The elongate muzzle 103 defines a longitudinal axis "X" and a lumen 111 extending longitudinally therethrough. The lumen 111 of the elongate muzzle 103 has a diameter such that the end effector assembly 20 and the shaft 18 of the surgical instrument 10 may be inserted through the lumen 111 of the elongate muzzle 103 in spaced relation to an inner peripheral surface of the elongate muzzle 103. The length of the elongate muzzle 103 is approximately the combined length of the shaft 18 and the end effector assembly 20 of the surgical instrument 10 to fully accommodate these components therein.

In some aspects, instead of the handle receiving portion 104 and the proximal section 106 of the shaft receiving portion 102 being detachably connected, the handle receiving portion 104 and the proximal section 106 of the shaft receiving portion 102 may be monolithically formed with one another. In such embodiments, the elongate muzzle 103 may be detachably coupled to the proximal section 106 of the shaft receiving portion 102.

In other aspects, each of the elongate muzzle 103 of the shaft receiving portion 102, the proximal section 106 of the shaft receiving portion 102, and the handle receiving portion 104 may be monolithically formed with one another. In these embodiments, the handle receiving portion 104 may have an opened proximal end 108 allowing for the selective receipt of the surgical instrument 10 therethrough. The proximal end 108 of the handle receiving portion 104 may have a door or cover (not shown) for closing the open proximal end 108 when the surgical instrument 10 is received in the cleaning fixture 100.

The proximal section 106 of the shaft receiving portion 102 includes a keying member 110 aligned with the elongate muzzle 103. The keying member 110 extends proximally from the proximal section 106 of the shaft receiving portion 102 and is configured to receive a cone-shaped, distal collar 13 (or other suitable component) of the handle 12 of the surgical instrument 10 to retain the surgical instrument 10 in a substantially fixed position within the cleaning fixture 100. In aspects, the keying member 110 may act as a fluid-tight seal between the handle 12 of the surgical instrument 10 and the cleaning fixture 100. It is contemplated that the keying member 100 may include a valve (not shown) that selectively opens via the control system 400 (FIG. 8) to allow for fluid to enter the shaft 18 of the surgical instrument 100 from the handle receiving portion 104. When the collar 13 of the surgical instrument 10 is seated into the keying member 110, the surgical instrument 10 is maintained in position where the central longitudinal axis of the shaft 18 of the surgical instrument 10 is disposed in substantially coaxial alignment with the central longitudinal axis "X" of the elongate muzzle 103 of the cleaning fixture 100. In some aspects, the keying member 110 may be configured to complement other types of distal collars to accommodate other surgical instruments within the cleaning fixture 100.

The shaft receiving portion 102 of the cleaning fixture 100 may further include a jaw-prop mechanism 118 extending perpendicularly through a distal end portion 115 of the elongate muzzle 103. The jaw-prop mechanism 118 has a rod-shaped actuator 122 extending through the elongate muzzle 103, and a foot 124 disposed at an end of the actuator 122. The actuator 122 is supported on the distal end portion 115 of the elongate muzzle 103 and is configured to slide relative thereto between a first position, in which the foot 124 of the jaw-prop mechanism 118 is disposed above (i.e., out of alignment) with the longitudinal axis "X" of the elongate muzzle 103, and a second position, in which the foot 124 of the jaw-prop mechanism 118 is aligned with the longitudinal axis "X" of the elongate muzzle 103 and, as such, in horizontal registration with the end effector assembly 20 of the surgical instrument 10. It is contemplated that the jaw-prop mechanism 118 may be actuated manually or automatically via hydraulics or in any other suitable manner, as further described below with reference to a lever activation assembly 140 of the cleaning fixture 100.

The foot 124 of the jaw-prop mechanism 118 may be a pair of splayed arms configured to maintain the jaw members 28a, 28b of the end effector assembly 20 propped open without inhibiting cleaning fluid from passing in and around the knife 22 of the surgical instrument 10 and, in embodiments, in channels (not explicitly shown) defined within the jaw members 28a, 28b for accommodating the knife 22 and/or the knife path passageway (not explicitly shown) allowing the knife 22 to move relative to the end effector assembly 20. The pair of splayed arms forming the foot 124 of the jaw-prop mechanism 118 may be spaced from one another a distance substantially equal to the distance between the jaw members 28a, 28b of the surgical instrument 10 when the jaw members 28a, 28b are in the open position. As such, when the foot 124 of the jaw-prop mechanism 118 is disposed between the jaw members 28a, 28b of the surgical instrument 10, the jaw members 28a, 28b are maintained in the open position to facilitate access of the cleaning fluid to the knife 22 of the surgical instrument 10 and surrounding areas within the end effector assembly 20.

The shaft receiving portion 102 of the cleaning fixture 100 may further include a plurality of nozzles or openings 136a, 136b disposed towards the distal end portion 115 of the elongate muzzle 103. The nozzles 136a, 136b may be operatively connected to a valve system 200 (FIG. 8) by one or more lines (not explicitly shown), although any other suitable connector(s) for delivering fluid to the nozzles 136a, 136b may be provided. The nozzles 136a, 136b act as inlets into the interior lumen 111 of the elongate muzzle 103. The nozzles 136a, 136b may be disposed annularly about the circumference of the elongate muzzle 103 to direct the flow of fluid from the nozzles 136a, 136b radially inwardly into the lumen 111 of the muzzle 103 and, in turn, radially about the end effector assembly 20. In some aspects, the nozzles 136a, 136b may be used to withdraw fluids from the interior of the cleaning fixture 100.

The elongate muzzle 103 may further include a distal nozzle 136c located on the closed distal end 117 thereof. The distal nozzle 136c is configured to direct the flow of fluid from the nozzle 136c coaxially along the longitudinal axis "X" of the elongate muzzle 103 in a proximal direction towards the knife 22 of the end effector assembly 20. It is contemplated that the elongate muzzle 103 may include any suitable number of nozzles provided in any suitable configuration. In addition to nozzles 136a, 136b, 136c providing cleaning fluid to the knife 22, the channels defined within the jaw members 28a, 28b for accommodating the knife 22, and/or the knife path passageway allowing the knife 22 to move relative to the end effector assembly 20, the nozzle 136c may be configured to direct cleaning fluid proximally through the end effector assembly 20 and the shaft 18 to flush the area within the shaft 18 and the components disposed within the shaft 18, e.g., the portion of the knife 22 proximally of the knife blade, a portion of the drive assembly 26, etc.

The shaft receiving portion 102 of the cleaning fixture 100 further includes a lever activation assembly 140 and a knife actuation assembly 150 each disposed on the proximal section 106 thereof. The lever activation assembly 140 has a lever 142, an actuator 144, and a nozzle 146. The lever 142 is positioned such that, when the surgical instrument 10 is disposed within the cleaning fixture 100, the lever 142 is nested between the arcuate segment 30a of the movable handle 30 and the proximal leg 30b of the movable handle 30. The lever 142 may have a vertical segment 142a configured to contact the arcuate segment 30a of the movable handle 30, and a horizontal segment 142b configured to contact the proximal leg 30b of the movable handle 30. The actuator 144 may be a cylinder such as a hydraulic cylinder, pneumatic cylinder, other suitable cylinder, or other suitable actuator.

The nozzle 146 of the lever activation assembly 140 is configured to be operatively connected to the valve system 200 (FIG. 8) by any suitable connector (not explicitly shown) to deliver fluid pressure to the actuator 144. When fluid is delivered from the valve system 200, through the nozzle 146, to the actuator 144, the actuator 144 is actuated and urges the lever 142 in a proximal direction from a first position to a second position. Such movement of the lever 142, in turn, actuates the moveable handle 30 of the surgical instrument 10 to thereby manipulate the end effector assembly 20 from the open position to the clamping position.

Ceasing the delivery of fluid, or a reduction of fluid delivery to the nozzle 146 (or otherwise releasing or returning the actuator), results in the lever 142 returning from the second position back to the first position and, thus, urging the moveable handle 30 to manipulate the end effector assembly 20 from the clamped position back to the open position. During some uses, when the foot 124 of the jaw-prop mechanism 118 is disposed between the jaw members 28a, 28b of the end effector assembly 20, a ceasing of delivery of fluid to the nozzles 146 does not result in a clamping of the jaw members 28a, 28b.

The amount and frequency of manipulation of the end effector assembly 20 is controlled via the fluid pressure cycle delivering fluid from the valve system 200 to the lever activation assembly 140 and may be selected based upon the particular configuration of the instrument, the type of cleaning being effected, experimental data, and/or other factors. As an alternative to a cylinder-based activation assembly 140, other suitable mechanisms, e.g., motors, may also be provided for mechanically urging movement of the movable handle 30. In some aspects, the lever activation assembly 140 may be manually actuated or actuated via any suitable mechanical actuator.

The knife actuation assembly 150 of the shaft receiving portion 102 is disposed above and in vertical registration with the lever activation assembly 140. In some aspects, the knife actuation assembly 150 may be misaligned with the lever activation assembly 140. The knife actuation assembly 150 is configured to selectively actuate the knife trigger assembly 16 of the surgical instrument 10 when the surgical instrument 10 is captured in the cleaning fixture 100 to assist in cleaning the knife blade of the knife 22 of the surgical instrument 10. The knife actuation assembly 150 includes a lever 152, an actuator 154, and a nozzle 156. The lever 152 is positioned such that, when the surgical instrument 10 is disposed within the cleaning fixture 100, the lever 152 is engaged with the trigger 34 of the knife trigger assembly 16 of the surgical instrument 10. The lever 152 may have an arcuate proximal edge 158 dimensioned to match the outer profile of the trigger 34.

The actuator 154 may be a cylinder such as a hydraulic cylinder, pneumatic cylinder, other suitable cylinder, or other suitable actuator. The nozzle 156 of the knife actuation assembly 150 is configured to be operatively connected to the valve system 200 by any suitable connector (not explicitly shown) to deliver fluid pressure to the actuator 154. When fluid is delivered from the valve system 200, through the nozzle 156, to the actuator 154, the actuator 154 is actuated and urges the lever 152 in a proximal direction. When the surgical instrument 10 is disposed within the cleaning fixture 100, actuation of the lever 152 of the knife actuation assembly 150 causes the proximal edge 158 of the lever 152 to urge the trigger 34 of the knife trigger assembly 16 of the surgical instrument 10 in a proximal direction, thereby translating the knife blade of the knife 22 from the retracted position to the extended position relative to the end effector assembly 20.

Ceasing the delivery of fluid, or a reduction of fluid delivery to the nozzle 156, results in the lever 152 moving distally away from the trigger 34 of the knife trigger assembly 16. As the lever 152 moves away from the knife trigger assembly 16, the resiliently biased trigger 34 of the knife trigger assembly 16 is allowed to move back to the unactuated position within the end effector assembly 20.

In aspects, prior to activating the knife actuation assembly 150 of the cleaning fixture 100, the jaw-prop mechanism 118 may be activated to maintain the end effector assembly 20 in the open position to allow for cleaning fluid to more readily contact the knife blade of the surgical instrument 10.

The amount and frequency of manipulation of the knife blade assembly 150 of the surgical instrument 10 is controlled via the fluid pressure cycle delivering fluid from the valve system 200 to the knife actuation assembly 150 of the cleaning fixture 100 and may be selected based upon the particular configuration of the instrument, the type of cleaning being effected, experimental data, and/or other factors. As an alternative to a cylinder-based activation assembly 150, other suitable mechanisms, e.g., motors, may also be provided for mechanically urging movement of the knife actuation assembly 150. In some aspects, the knife actuation assembly 150 may be manually actuated or actuated via any suitable mechanical actuator.

The handle receiving portion 104 of the cleaning fixture 100 is configured to receive the housing 12, the handle assembly 14, and the knife trigger assembly 16 of the surgical instrument 10. The handle receiving portion 104 is illustrated as having a squared configuration, but it is contemplated that the handle receiving portion 104 may assume any suitable shape, such as, for example, rounded, or conform to the outer surface of the housing 12 of the surgical instrument 10. The handle receiving portion 104 may include one or more flushing ports 160 operatively connected to any suitable connector, e.g., a hose, to carry fluid from cleaning fixture 100 to a drain or other outlet (not explicitly shown).

Figure 8:
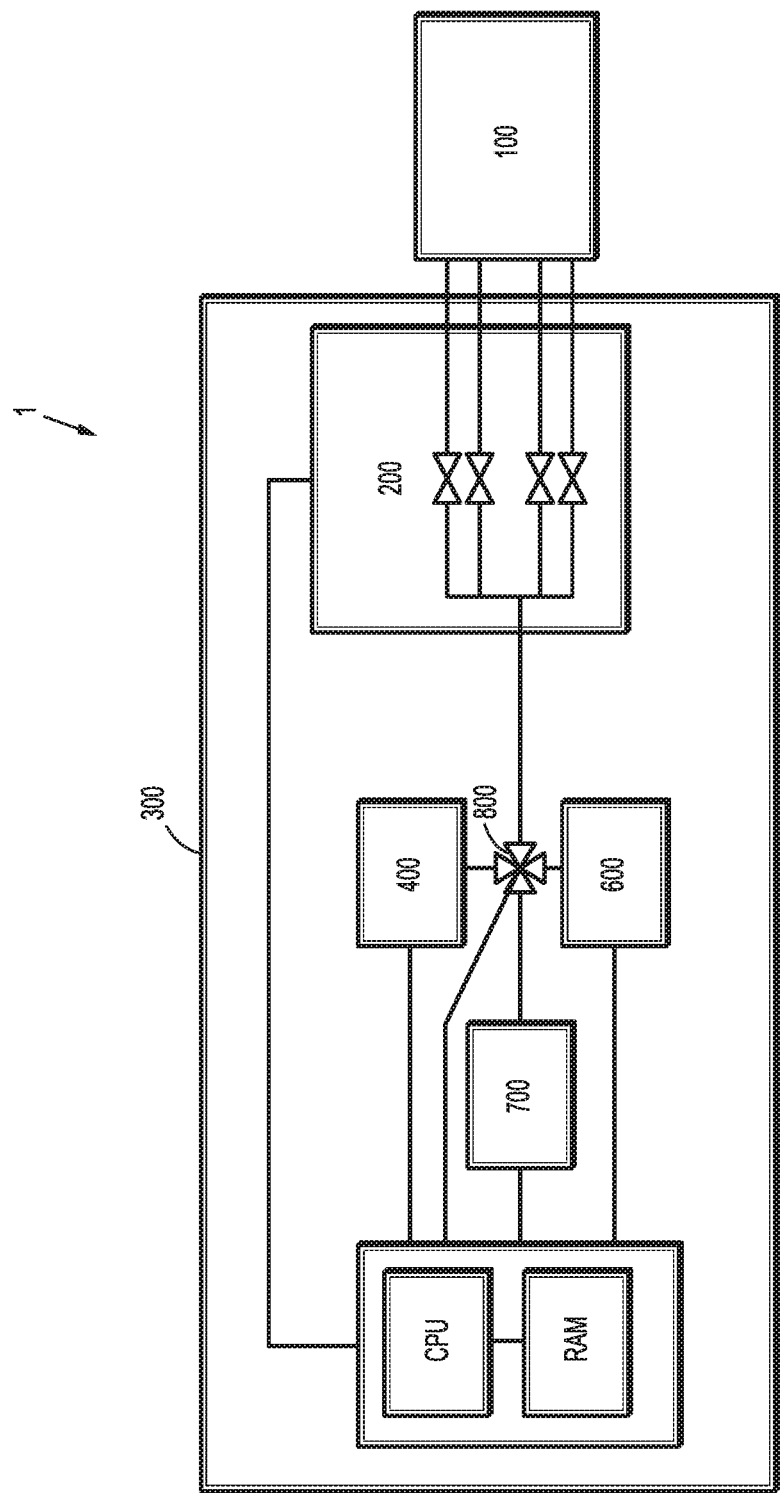
FIG. 8 is a schematic diagram of a cleaning system for cleaning surgical instruments provided in accordance with the present disclosure.

With reference to FIG. 8, illustrated is a cleaning system 1 that includes the cleaning fixture 100 and a control box 300 operatively connected to the cleaning fixture 100. In some aspects, the control box 300 is configured to connect to a plurality of cleaning fixtures 100 to facilitate simultaneous cleaning of multiple surgical instrument (similar or different). However, for purposes of simplicity, the control box 300 is described herein as configured for use with a single cleaning fixture 100.

The control box 300 includes the valve system 200, a dosage control system 400, an air supply 600, a vacuum source 700, and a multidirectional valve 800. The dosage control system 400 is coupled to a fluid supply, e.g., a water supply (not shown), for mixing with one or more chemicals, cleaning compounds, etc. stored within or input into the dosage control system 400. Such chemicals and cleaning compounds may include, for example, enzymatic compounds, detergents, disinfectants, etc. The dosage control system 400 may additionally be configured to simply provide the fluid from the fluid supply without adding any chemicals, e.g., during a flushing or rinsing stage, and may further include one or more heaters (not specifically shown) for heating the fluid and/or mixture to be supplied to a desired temperature to facilitate cleaning.

The control box 300 further includes a CPU and memory, e.g., a RAM, that executes and stores one or more cleaning programs, respectively. The CPU is operatively connected to the valve system 200, the dosage system 400, the air supply 600, the vacuum source 700, and the multidirectional valve 800. The multidirectional valve 800 may be configured as a four way ball valve, although any other suitable valve may be provided including multidirectional valves different in number. The multidirectional valve 800 is operatively connected to the valve system 200, the air supply 600, and the vacuum source 700. It is envisioned that during execution of the cleaning program, the multidirectional valve 800 will switch between two of more of: supplying the valve system 200 with the mixture from the dosage system 400, supplying air from the air supply 600, and removing moisture, fluids, and/or residue with the vacuum source 700. During use, the CPU may direct the dosage system 400 to provide an appropriate mixture of fluid and/or chemicals, cleaning compounds, etc., depending upon the cleaning program. Alternatively, the dosage system 400 may include separate control electronics for these purposes.

The valve system 200 includes four valves; however, the number of valves may vary. Each valve included in the valve system 200 may be operatively connected to the nozzles 136a-c, the jaw-prop mechanism 118, the lever activation assembly 140, and the knife actuation assembly 150 of the cleaning fixture 100. The valve system 200 supplies the cleaning fixture 100 with the chemical/fluid mixture or a fluid (e.g., water or air), depending on the particular stage of the cleaning program.

The use and operation of the cleaning fixture 100 for cleaning the surgical instrument 10 will now be described. Although detailed with respect to the cleaning fixture 100 and the surgical instrument 10 for exemplary purposes, the methods detailed herein are equally applicable for use with other cleaning fixtures and/or for cleaning other medical devices. As noted above, the control box 300 controls the various different stages of cleaning, although any or all of the cleaning stages may alternatively be controlled via any other suitable control and/or may be manually controlled.

The handle receiving portion 104 and the shaft receiving portion 102 of the cleaning fixture 100 are detached from one another. The shaft 18 and end effector assembly 20 of the surgical instrument 10 are received in the shaft receiving portion 102 of the cleaning fixture 100 and the collar 13 of the surgical instrument 10 is engaged with the keying member 110 of the cleaning fixture 100. With the surgical instrument 10 secured to the shaft receiving portion 102, the handle receiving portion 104 of the cleaning fixture 100 is positioned over the handle 12 of the surgical instrument 10 and is attached to the shaft receiving portion 102 to enclose the surgical instrument 10 within the cleaning fixture 100.

After enclosing the surgical instrument 10 in the cleaning fixture 100, the desired cleaning cycle is selected and initiated, e.g., by an operator pushing a button, touch screen, or other activator. As can be appreciated, in embodiments where the cleaning fixture 100 is configured to clean various different surgical instruments used in different procedures, different cleaning programs may be provided depending on the particular situation. The CPU of the control box 300 receives the initiation signal corresponding to the selected cleaning program and, in response, initiates that cleaning program.

Once activated, the dosage control system 400, under direction of the CPU, draws water (or other fluid), and the appropriate chemical(s), compounds, etc. into the dosage control system 400 and creates a mixture. The mixture is then supplied from the dosage control system 400 to the valve system 200. The valve system 200 delivers the mixture to the cleaning nozzles 136a-c, which direct the mixture initially into contact with and through the end effector assembly 20. The mixture passes through the lumen 111 of the elongate muzzle 103 and within the end effector assembly 20 and the shaft 18 to clean both the exterior and interior of the end effector assembly 20 and the shaft 18 of the surgical instrument 10, ultimately entering the handle receiving portion 102 of the cleaning fixture 100 (e.g., via the valve of the keying member 110) to clean the housing 12, the handle assembly 14, and the knife trigger assembly 16 of the surgical instrument 10.

In some aspects, the cleaning nozzles 136a-c may be configured to direct the mixture through the shaft 18 of the surgical instrument 10, whereby the fluid enters the housing 12 to clean the interior of the housing 12 and then exits the surgical instrument 10 to enter the handle receiving portion 104 of the cleaning fixture 100 and out of the cleaning fixture 100 via the ports 160.

In aspects, the valve system 200 may be fluidly coupled to the port 160 of the cleaning fixture 100 to first deliver cleaning fluid into the handle receiving portion 104 of the cleaning fixture 100. Accordingly, with the valve of the keying member 110 closed, the cleaning fluid may be directed from the port 160 into the handle receiving portion 104 of the cleaning fixture to pressurize the interior of the handle receiving portion 104 until the cleaning fluid is forced through various openings in the housing 12 of the surgical instrument 10. Upon the pressurized cleaning fluid entering the housing 12, the cleaning fluid is forced distally through the shaft 18, into the end effector assembly 20, and out of the cleaning fixture 100 via the ports 136a-c. The exterior of the surgical instrument 100 may be similarly cleaned by opening the valve of the keying member 110 to allow the cleaning fluid to pass around the exterior of the handle 12, travel through the valve of the keying member 110 into the muzzle 103, over the shaft 18 and the end effector assembly 20, and out of the cleaning fixture 100 via the ports 136a-c.

In addition to supplying the mixture to the cleaning nozzles 136a-c of the cleaning fixture 100, the valve system 200 may also deliver the mixture to the lever activation assembly 140 to actuate the lever activation assembly 140. Alternatively to using the valve system 200 to actuate the lever activation assembly 140, the lever activation assembly 140 may be actuated by a motor or other suitable mechanism, including a manual actuation. An actuation of the lever activation assembly 140 causes the end effector assembly 20 of the surgical instrument 10 to move between the open and clamped positions, via the mechanical process described above. The lever activation assembly 140 may be cyclically activated and deactivated to effect a cyclic opening and closing of the end effector assembly 20, which facilitates cleaning thereof.

The valve system 200 may also supply the mixture to the knife actuation assembly 150 of the cleaning fixture 100 to actuate the knife trigger assembly 16 of the surgical instrument 10. Alternatively to using the valve system 200 to actuate the knife actuation assembly 150, the knife actuation assembly 150 may be actuated by a motor or other suitable mechanism, including a manual actuation. An actuation of the knife actuation assembly 150 actuates the knife trigger assembly 16 of the surgical instrument 10, via the mechanical process described above. Actuation of the knife trigger assembly 16 of the surgical instrument 10 moves the knife blade of the knife 22 of the surgical instrument 10 distally through the end effector assembly 20. The knife actuation assembly 150 may be cyclically activated and deactivated to effect a cyclic advancement and retraction of the knife blade of the knife 22, which facilitates cleaning thereof. The valve system 200 may be configured to supply the cleaning fluid through the opening 136c of the cleaning fixture 100 toward the knife 22 as the knife 22 is being advanced through the end effector assembly 20.

In some cleaning cycles, it may be beneficial to maintain the jaw members 28a, 28b of the end effector assembly 20 in the open position while cleaning the knife blade of the surgical instrument 10. To accomplish this, the control box 300 may be configured to actuate the jaw-prop mechanism 118 of the cleaning fixture 100 after having activated the lever activation assembly 140. Actuation of the jaw-prop mechanism 118 positions the foot 124 thereof between the jaw members 28a, 28b of the end effector assembly 20, maintaining the jaw members 28a, 28b in the open position. In some aspects, instead of using the jaw-prop mechanism 118, the control box 300 may be configured to hold the lever activation assembly 140 in the unactuated position (i.e., a distal position) to maintain the jaw members 28a, 28b of the surgical instrument 10 in the open position. As the jaw members 28a, 28b of the end effector assembly 20 are held in the open position, the knife actuation assembly 150 of the cleaning fixture 100 is actuated to ultimately effect the distal advancement of the knife blade of the knife 22 of the surgical instrument 10. The cleaning mixture may then be supplied to the cleaning fixture 100 via the nozzles 136a-c to clean the now-exposed, distally advanced knife blade of the knife 22.

In one embodiment, the surgical instrument 10 may have the safety feature described above by which the knife trigger assembly 16 cannot be actuated until after the handle assembly 14 is actuated. However, as previously described, it is desirable to clean the knife 22 of the surgical instrument 10 while the jaw members 28a, 28b are in a spaced-apart position. Accordingly, to bypass this safety feature, the handle assembly 14 is actuated (e.g., via the level activation assembly 140 of the cleaning fixture 100) until the threshold compressive force is reached. The threshold compressive force decouples the movable handle 30 of the handle assembly 14 from the end effector assembly 20. As such, further movement of the movable handle 30 toward the compressed state is permitted despite the jaw members 28a, 28b being held in the open position. After the movable handle 30 is moved to the compressed state, the knife actuation assembly 150 of the cleaning fixture 100 may be actuated (e.g., via the valve system 200) to actuate the knife trigger assembly 16 of the surgical instrument 10, thereby advancing the knife 22 through the spaced-apart jaw members 28a, 28b. At this point, the valve system 200 may then supply the cleaning fluid to the knife 22.

The valve system 200, under direction of the CPU, controls the amount of mixture delivered, the pressure at which the mixture is delivered, and the temperature the mixture is delivered to the nozzles 136a-c, the lever activation assembly 140, and the knife actuation assembly 150. The CPU may also control the separate and/or independent actuation of the lever activation assembly 140 and the knife actuation assembly 150 where a motor or other suitable mechanism is utilized to actuate the lever activation assembly 140 and the knife actuation assembly 150.

Draining of the mixture and/or fluid within the cleaning fixture 100 may be effected via opening the one or more flushing ports 160 of the handle receiving portion 104 of the cleaning fixture 100 and/or supplying water to the cleaning fixture 100. In some aspects, the control system 400 may be configured to recycle the cleaning fluid while filtering the cleaning fluid after each pass through the cleaning fixture 100. The cleaning fixture may have sensors configured to detect the number of particles within the cleaning mixture to determine the state of cleanliness of the system.

Depending upon the particular cleaning program employed, these steps may be repeated any number of times in any order to, for example, provide multiple stages of cleaning (with the same or different chemical mixtures), enable flushing between stages of cleaning, or for other purposes.

Following the cleaning and rinsing stages detailed above, the multidirectional valve 800 is manipulated and the air supply 600 activated to supply air to the cleaning fixture 100 (through the various nozzles thereof) to dry the enclosed surgical instrument 10. The air supplied to the cleaning fixture 100 may be ambient temperature or heated, depending on a particular purpose or cleaning protocol. In some aspects, heaters may be implemented to facilitate drying of the handle receiving portion 104 of the cleaning fixture 100.

Following the cleaning, rinsing, and air supply stages (or intermediate thereof, e.g., as a final component of the drying stage), the multidirectional valve 800 is manipulated and the vacuum source 700 is activated, such that a vacuum is created to remove any cleaning residue, residual moisture, and/or other fluids from the cleaning fixture 100. At the completion of cleaning and drying, the surgical instrument 10 is removed from the cleaning fixture 100 and may be reassembled for further use or repackaged.

Figure 9:
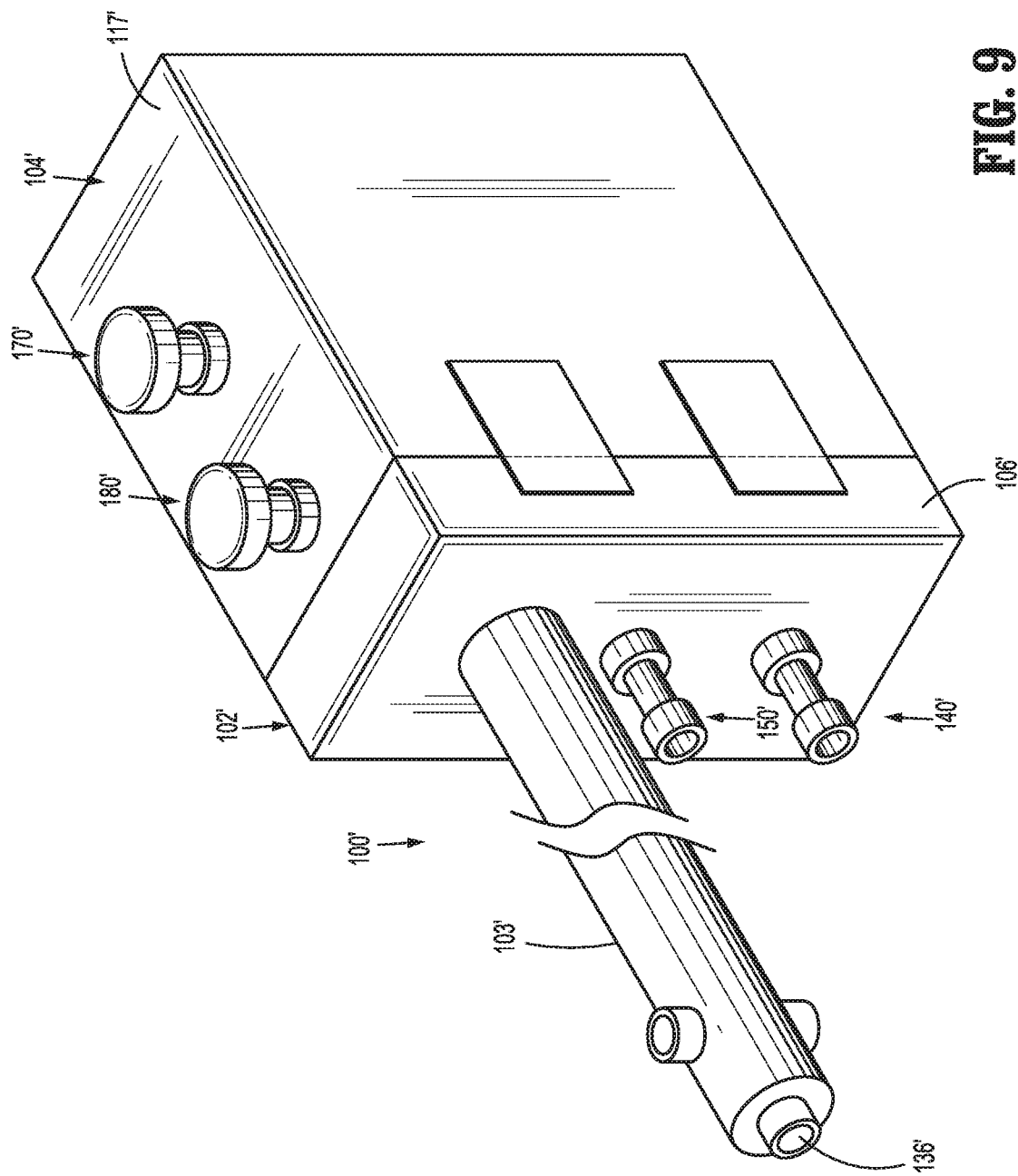
FIG. 9 is a side perspective view of another exemplary embodiment of a cleaning fixture for cleaning the surgical instrument of FIGS. 3-5.
Figure 10:
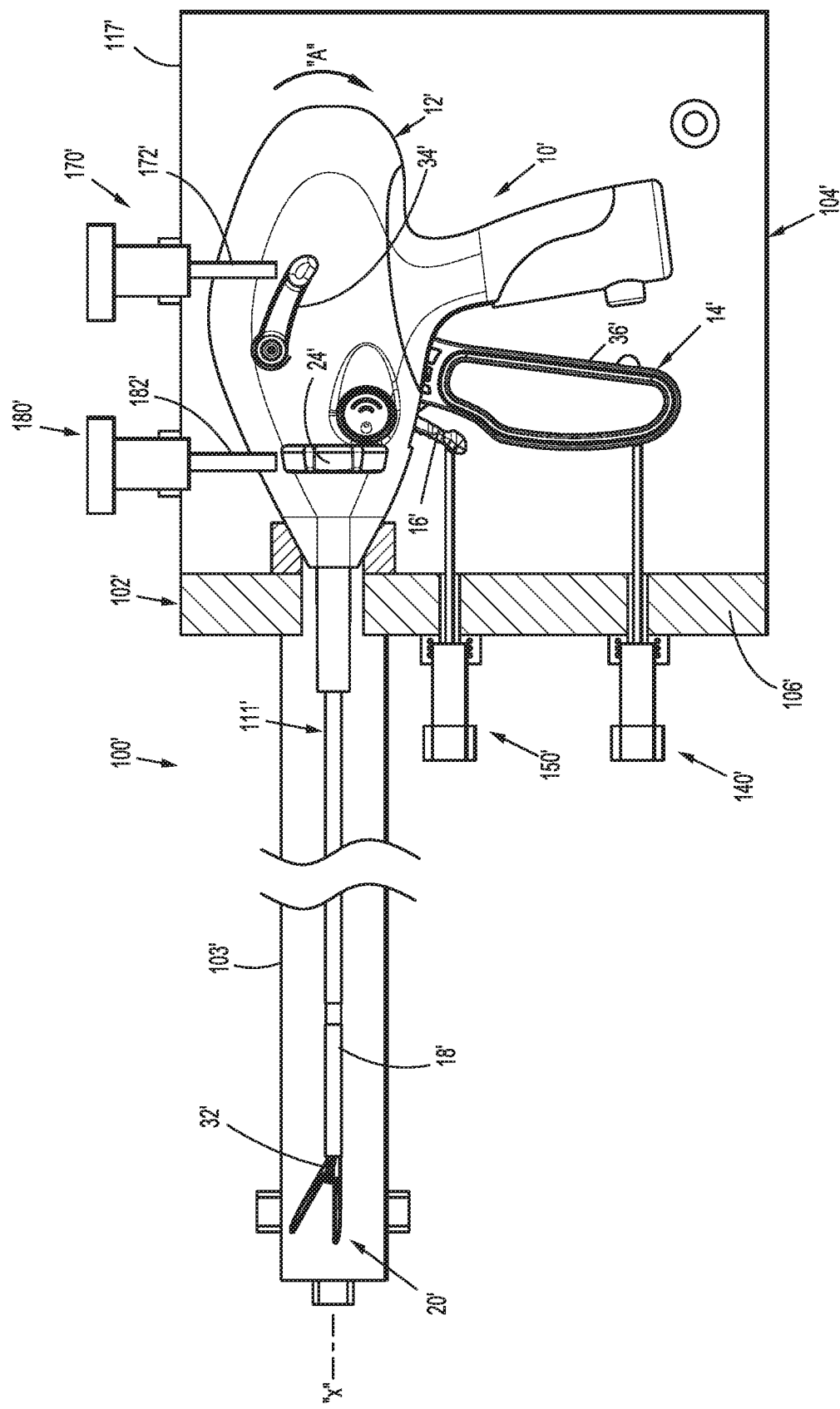
FIG. 10 is a side cross-sectional view of the cleaning fixture of FIG. 8, with the surgical instrument of FIGS. 3-5 disposed therein.

With reference to FIGS. 9-10, another embodiment of a cleaning fixture 100' is illustrated, similar to the cleaning fixture 100 described above. Due to the similarities between the cleaning fixture 100' of the present embodiment and the cleaning fixture 100 described above, only those elements of the cleaning fixture 100' deemed necessary to elucidate the differences from the cleaning fixture 100 described above will be described in detail.

The cleaning fixture 100' is shown housing surgical instrument 10' therein (FIGS. 3-5) for cleaning of the surgical instrument 10'. However, in some aspects, the cleaning fixture 100' may similarly be configured for use with any other suitable surgical instrument. Different configurations and considerations apply in providing a cleaning fixture 100' for a particular type of surgical instrument; however, the aspects and features of the present disclosure remain generally consistent regardless of the particular surgical instrument for which the cleaning fixture 100' is configured. It is also contemplated that a generic cleaning fixture be provided to enable cleaning of any one of a variety of different surgical instruments. Such a generic cleaning fixture may include interchangeable and/or adaptable components configured to achieve various different configurations to accommodate various different surgical instruments.

The cleaning fixture 100' generally includes a shaft receiving portion 102' and a handle receiving portion 104'. The shaft receiving portion 102' and the handle receiving portion 104', when connected, cooperate to define an enclosure for retaining the housing 12', the handle assembly 14', the knife trigger assembly 16', and the deployment and retraction mechanism 34' of the surgical instrument 10', as detailed below. The shaft receiving portion 102' extends distally from the handle receiving portion 104' and includes an elongate muzzle 103'. The elongate muzzle 103' extends distally from a proximal section 106' of the shaft receiving portion 102'. The elongate muzzle 103' defines a longitudinal axis "X" and defines a lumen 111' extending longitudinally therethrough. The lumen 111' of the elongate muzzle 103' has a diameter dimensioned such that the end effector assembly 20' and the shaft 18' of the surgical instrument 10' may be inserted through the lumen 111' of the elongate muzzle 103' in spaced relation to an inner peripheral surface of the elongate muzzle 103'.

The shaft receiving portion 102' of the cleaning fixture 100' further includes a lever activation assembly 140' and a knife actuation assembly 150', which are substantially similar or the same as the respective lever activation assembly 140 and the knife actuation assembly 150 of the cleaning fixture 100 of FIGS. 6 and 7. The lever activation assembly 140' is configured to actuate the movable handle 36' of the surgical instrument 10' to thereby manipulate the end effector assembly 20' from the open position to the clamping position. In aspects of the present disclosure, the cleaning fixture 100' may include a jaw-prop mechanism (not shown), similar to the jaw-prop mechanism 118 above, for maintaining the end effector assembly 20' in the open position.

The knife actuation assembly 150' of the shaft receiving portion 102' is disposed above and in vertical registration with the lever activation assembly 140'. The knife actuation assembly 150' is configured to selectively actuate the knife trigger assembly 16' of the surgical instrument 10' when the surgical instrument 10' is captured in the cleaning fixture 100' to assist in cleaning the knife blade of the surgical instrument 10'.

The cleaning fixture 100' further includes a monopolar actuation assembly 170' movably coupled to an upper surface 117' of the handle receiving portion 104' of the cleaning fixture 100'. The monopolar actuation assembly 170' is configured to selectively actuate the deployment and retraction mechanism 34' of the surgical instrument 10 when the surgical instrument 10' is captured in the cleaning fixture 100' to assist in cleaning the monopolar assembly 32' of the surgical instrument 10'. The monopolar actuation assembly 170' may be configured similarly as the knife actuation assembly 150 of cleaning fixture 100. As such, when the surgical instrument 10' is disposed within the cleaning fixture 100', actuation of the monopolar actuation assembly 170' causes a lever 172' thereof to urge the deployment and retraction mechanism 34' of the monopolar assembly 32' of the surgical instrument 10' in a clockwise direction, indicated by arrow "A" in FIG. 10, thereby translating the monopolar assembly 32' of the surgical instrument 10' from the retracted position to the extended position relative to the end effector assembly 20'.

The valve system 200 (FIG. 8) may be configured to supply the cleaning fluid through an opening 136' in the elongate muzzle 103', or any other suitable access opening in the cleaning fixture 100,' toward the monopolar assembly 32' of the surgical instrument 10' as the energizable member 40' and the insulative sheath 44' of the monopolar assembly 32' are being advanced relative to the end effector assembly 20.

In some aspects of the present disclosure, the cleaning fixture 100' may further include a knob actuation assembly 180' disposed adjacent the monopolar actuation assembly 170'. It is contemplated that the knob actuation assembly may be substantially similar or the same as the monopolar actuation assembly 170'. The knob actuation assembly 180' is configured to effect a rotation of the rotating assembly 24' of the surgical instrument 10'. The knob actuation assembly 180' may have a geared end 182' for intermeshing with the teeth of the rotating assembly 24'. As such, vertical movement of the knob actuation assembly 180' in either direction effects a corresponding rotation of the rotating assembly 24' of the surgical instrument 10'. Rotating the rotating assembly 24' of the surgical instrument 10' assists in cleaning the end effector assembly 20', the shaft 18', and the rotating assembly 24'.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limited, but merely as exemplifications of particular embodiments. Those skilled in the art will envision other modifications within the scope and spirit of the claims appended hereto.

What is claimed is:

1. A cleaning fixture for a surgical instrument, the cleaning fixture comprising:
    a handle receiving portion configured to receive a housing of a surgical instrument;
    a shaft receiving portion extending distally of the handle receiving portion and configured to receive a shaft and an end effector assembly of the surgical instrument, the shaft receiving portion including an elongate muzzle defining a longitudinal axis and a lumen configured to house the shaft and the end effector assembly of the surgical instrument;
    a knife actuation assembly movably coupled to the handle receiving portion or the shaft receiving portion, wherein the knife actuation assembly is configured to selectively actuate a knife trigger assembly of the surgical instrument to advance a knife of the surgical instrument between jaw members of the end effector assembly thereof; and
    a jaw-prop mechanism movably coupled to a distal end portion of the elongate muzzle, the jaw-prop mechanism including a foot disposed in the lumen of the elongate muzzle and configured to maintain the end effector assembly of the surgical instrument in an open position.

2. The cleaning fixture according to claim 1, wherein the knife actuation assembly includes a lever protruding into the handle receiving portion, the lever being movable relative to the handle receiving portion to actuate the knife trigger assembly of the surgical instrument.

3. The cleaning fixture according to claim 2, wherein the lever has a proximal end configured to contact the knife trigger assembly of the surgical instrument.

4. The cleaning fixture according to claim 1, wherein the handle receiving portion is releasably securable with the shaft receiving portion to enclose the surgical instrument therein.

5. The cleaning fixture according to claim 1, wherein the shaft receiving portion further includes a proximal section releasably coupled to a distal section of the handle receiving portion, the elongate muzzle extending distally from the proximal section.

6. The cleaning fixture according to claim 1, wherein the shaft receiving portion defines an opening disposed towards a distal end portion of the elongate muzzle, such that the opening is positioned adjacent the end effector assembly of the surgical instrument upon receipt of the shaft and end effector assembly of the surgical instrument within the shaft receiving portion.

7. The cleaning fixture according to claim 6, wherein the opening is configured to facilitate the passage of a cleaning fluid proximally through the elongate muzzle to flush the lumen thereof.

8. The cleaning fixture according to claim 6, wherein the opening is configured to facilitate the passage of a cleaning fluid proximally towards the knife of the surgical instrument while the knife actuation assembly is actuated.

9. The cleaning fixture according to claim 1, further comprising a lever activation assembly movably coupled to the handle receiving portion or the shaft receiving portion, wherein the lever activation assembly is configured to selectively actuate a handle assembly of the surgical instrument.

10. The cleaning fixture according to claim 9, wherein the knife actuation assembly is disposed between an elongate muzzle of the shaft receiving portion and the lever activation assembly.

* * * * *